United States Patent [19]

Rivers

[11] Patent Number: 5,629,164
[45] Date of Patent: May 13, 1997

[54] ENZYME IMMUNOASSAY DEVICE

[75] Inventor: Douglas B. Rivers, Birmingham, Ala.

[73] Assignee: Southern Research Institute, Birmingham, Ala.

[21] Appl. No.: 981,243

[22] Filed: Nov. 25, 1992

Related U.S. Application Data

[63] Continuation of Ser. No. 612,794, Nov. 14, 1990, abandoned.

[51] Int. Cl.⁶ ........................................ G01N 33/53
[52] U.S. Cl. .................. 435/7.9; 435/7.92; 435/7.93; 435/969; 435/970; 436/807; 436/810; 436/524; 436/527; 422/60; 422/58
[58] Field of Search .................... 435/7.9, 7.92, 435/7.93, 14, 805, 970, 929, 969; 436/807, 810, 524, 527; 422/56, 58, 60

[56] References Cited

U.S. PATENT DOCUMENTS

| | | | |
|---|---|---|---|
| 4,687,732 | 8/1987 | Ward et al. | 435/7.9 X |
| 4,717,656 | 1/1988 | Swanljung | 435/7.9 X |
| 4,826,759 | 5/1989 | Guire et al. | 422/58 X |
| 4,837,395 | 6/1989 | Leeder et al. | 435/7.9 X |
| 4,943,522 | 7/1990 | Eisinger et al. | 435/7.21 |
| 4,962,043 | 10/1990 | Nagase et al. | 422/58 X |
| 4,963,325 | 10/1990 | Lennon et al. | 422/58 X |
| 5,077,210 | 12/1991 | Eigler et al. | 436/524 X |

*Primary Examiner*—Carol A. Spiegel
*Attorney, Agent, or Firm*—Yahwak & Associates

[57] ABSTRACT

The present invention relates to an enzyme reagent ticket for conducting diagnostic or serological tests. More particularly, the present invention relates to an enzyme reagent device which allows for a low-cost, disposable, rapid and convenient system for use in the determination of various components in test fluids, and to a diagnostic kit including the device according to the present invention for conducting certain immunochemical, diagnostic or serological testing.

22 Claims, 3 Drawing Sheets

FIG. 3 ed as indicated by the arrows in FIGS. 2B and 2D to

ENZYME IMMUNOASSAY DEVICE

This is a continuation of my earlier U.S. patent application Ser. No. 612,794, filed Nov. 14, 1990, now abandoned.

Rapid diagnostic tests allowing for the qualitative and quantitative determination of a number of differing analytes hold great potential for acceptance by both laboratory and field personnel. In the clinical laboratory, rapid, sensitive, specific and accurate tests based upon the presence or absence of analyte in biological specimens provide possibilities for the early detection, confirmed diagnosis, and prompt treatment for many pathological conditions. In the field, the potential use of such tests may be extended to determine the presence or absence of differing analytes in air, food, water or soil.

The benefits and acceptance of the diagnostic devices and kits to perform such rapid analysis depends on a number of factors such as sensitivity, specificity, cost per test, ease of use, and timeliness of test results. Ideally, to be accepted by the user, such a device or kit should be simple to perform with rapid, easy to interpret and virtually foolproof results. In addition, such a device should be easily transportable, capable of providing the results of the test "on site", and disposable after use.

Three such attempts to provide for rapid diagnostic apparatus and kits are described in U.S. Pat. No. 3,697,227 to Goldstein et al, U.S. Pat. No. 4,717,656 to Swanljung, in U.S. Pat. No. 4,826,759 to Guire et al.

The United States Patent to Goldstein is directed to a disposable sampler for testing for the presence of constituents such as arsenic, sulfur or lead in air and water. However, the apparatus as defined in this patent may also be modified for clinical applications by using clinical specimens and altering the test reagents in the sampler. The sampler described by Goldstein comprises a laminated package having relatively impermeable base and retainer sheets wherein the base sheet is adapted to hold a fluid. In use, a sample of fluid (liquid or air) is injected into the sampler where the presence of the sought after analyte in the sample brings about a reaction with the reagent contained within the sampler to provide a visual signal.

The United States Patent to Swanljung describes an apparatus for performing a chemical analysis wherein all chemically active parts necessary for carrying out the desired analysis are built into the apparatus. Thus liquid samples and reagents need not be transferred between tubes, cups or other holders. Instead, the samples, reagents and reagent washes are contained on the surfaces of the apparatus, and these surfaces are arranged or mounted in such a manner that they may be contacted with the sample and with each other by simply folding the apparatus upon itself.

The United States Patent to Guire describes a field assay apparatus for the chemical analysis of an analyte in which a support strip carries bibulous elements upon its surface in such a manner that when the support is folded the elements are brought in contact with each other allowing fluid in one element to be expressed into another element.

In addition to these patented test devices, reagent strip test devices have also been developed and may be found in commercial use. Using such devices requires only that the technician dip the test strip into a sample and to note any visual response on the "dip stick". Usually this response is a specific color change wherein the intensity of the color within a specific time period is indicative of the presence and concentration of a particular component in the sample. A number of "dip sticks" are described in U.S. Pat. Nos. 3,125,443, 3,212,855, 3,814,668, 3,298,789, 4,618,475, and 4,774,054.

Even in view of the many devices appearing in the prior art, there is still the need for improved devices for conducting immunochemical, diagnostic or serological tests upon samples. There is especially a continuing need to be able to conduct such tests quickly at the location where the samples are obtained rather than collecting and forwarding such samples to a central laboratory for analysis. The present invention relates to devices for use in such tests. More particularly, the present invention relates to an enzyme reagent ticket which allows for a low-cost, disposable, rapid and convenient system for use in the determination of various components in test fluids.

The various aspects, advantages and features of the present invention will become apparent to, and more fully understood by, those skilled in the art by reference to the following detailed description of the invention taken in conjunction with the accompanying figures and examples which are provided for this purpose, and not for the purpose nor intention of limiting the scope of the invention, in which:

FIG. 1 (A–D) is a plan view of a first embodiment of the enzyme ticket device according to the present invention and showing its sequential use;

FIG. 2 (A–E) is a plan view of a second embodiment of an enzyme ticket device according to the present invention and showing its sequential use.

As seen in FIG. 1, the device 10 according to the present invention comprises a generally rectangular enzyme reagent card, support or ticket 11 having a fold or score line 16 dividing the ticket into two generally mirror image halves capable of being folded (as in FIG. 1B) upon themselves. The ticket has at least two (12 and 14), but preferably at least four (12, 13, 14, and 15), generally circular openings. Whereas any readout openings such as 14 and 15 extend partially through the ticket, any sample openings such as 12 and 13 extend completely through the ticket. When folded as indicated by the arrow in FIG. 1B upon score or fold 16 to produce the resulting folded ticket shown in FIG. 1C, the ticket is so designed that opening 12 will direct overlay its opposing opening 14, and opening 13 will directly overlay its opposing opening 15. That is, the openings are located on either side of the fold 16 such that they will be intersected along a diameter by a plane passing at right angles through the support and fold 16. Each opening in ticket 11 contains a disk or pad which can be seen in detail in FIG. 3. Thus, opening 12 contains disk 120 when viewed from the front of ticket 11 and a second disk 121 when viewed from the back of ticket 11; opening 13 contains disk 130 when viewed from the front of ticket 11 and a second disk 131 when viewed from the back of ticket 11; opening 14 contains disk 140, and opening 15 contains disk 150. In this embodiment, disks 140 and 150 are readout disks, disks 120 and 130 are antibody disks, and disks 121 and 131 are conjugate disks.

An alternate embodiment to device 10 is depicted by the device 20 in FIG. 2. More specifically, FIG. 2 shows a enzyme reagent card or ticket 21 having fold or score lines 24a and 24b dividing ticket 21 into three equal portions 1, 2 and 3 and allowing ticket 21 to be folded upon itself in thirds. Thus, line 24a lies between portion 1 and 2 and allows portion 1 to be folded over upon portion 2 as depicted in FIG. 2B; line 24b lies between portion 2 and 3 and allows portion 3 to be folded over upon portion 2 as depicted in FIG. 2D. Ticket 21 has three openings 22, 23 and 24 (although other duplicate sets of openings may be carried on the same ticket, each set being used for a different sample for analysis) extending partially through ticket 21. When folded upon score line 24a (as shown in FIG. 2B) the ticket is so designed that the opening 24 in portion 1 will directly overlay its opposing opening 23 in portion 2. When folded upon score line 24b (as shown in FIG. 2D) the ticket is so designed that the opening 22 in portion 3 will directly overlay its opposing opening 23 in portion 2. Opening 22 contains readout disk 220, opening 23 contains antibody disk 230, and opening 24 contains conjugate disk 240.

Figure 1A:
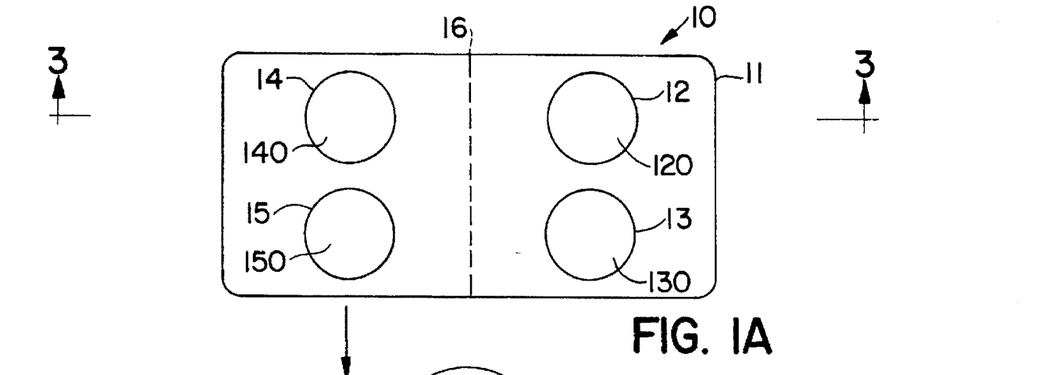
Figure 1B:
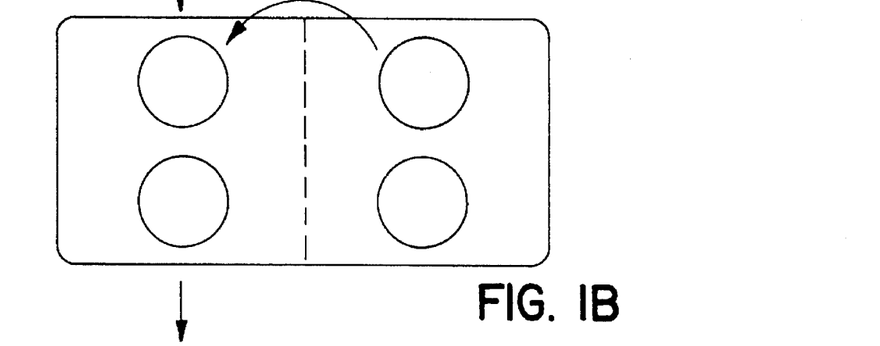
Figure 1C:
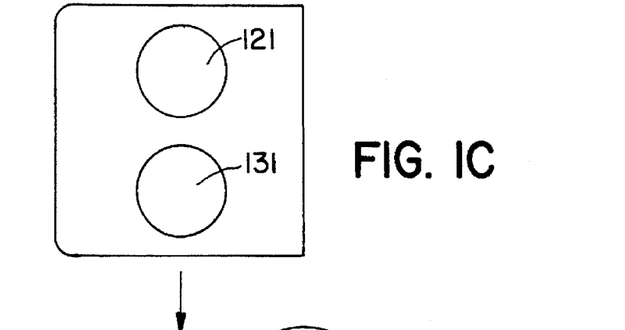
Figure 1D:
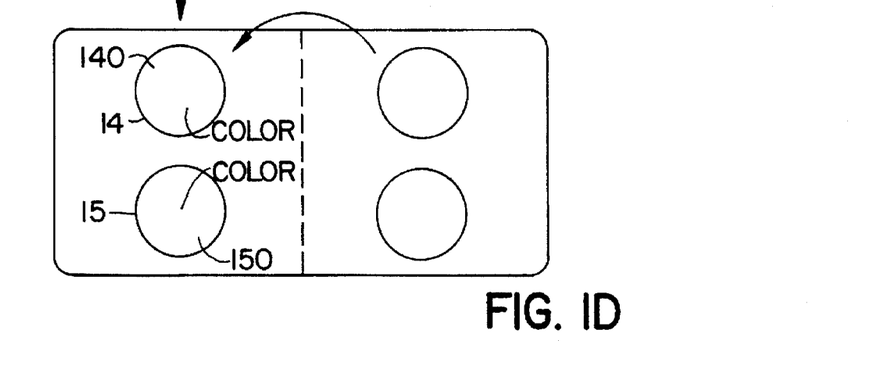
Figure 2A:
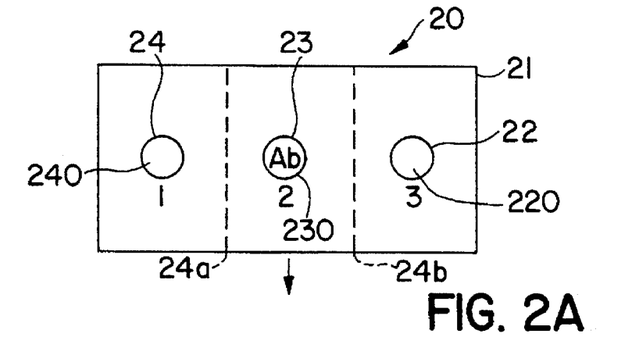
Figure 2B:
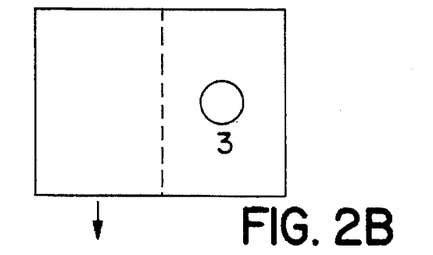
Figure 2C:
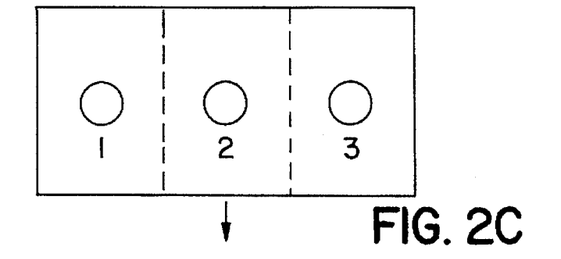
Figure 2D:
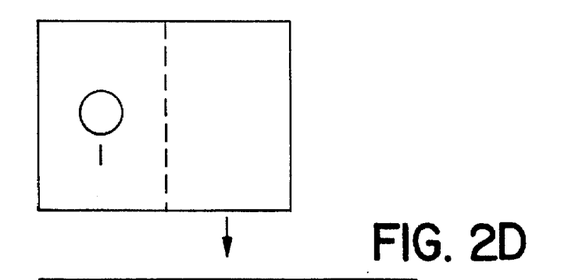
Figure 2E:
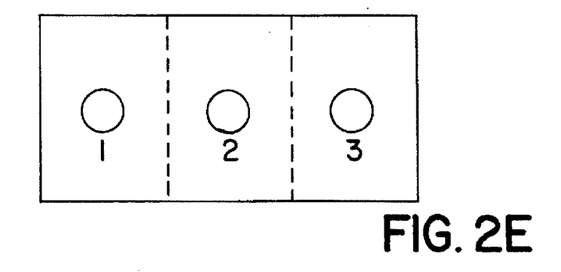
Figure 3:
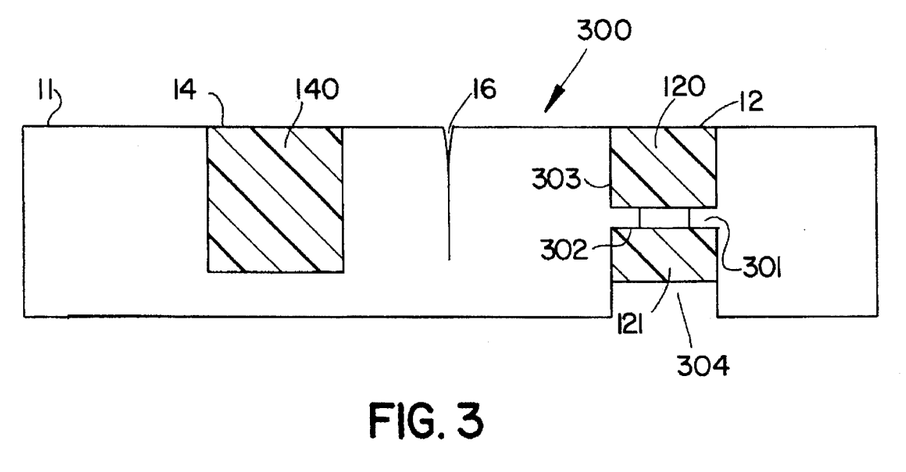
FIG. 3 is a cross section view taken along the lines 3—3 of FIG. 1.

In the cross sectional depiction of FIG. 3 (which also corresponds to a depiction taken through a parallel plane to 3—3 which passes through openings 14-12), which is greatly enlarged for purposes of illustration only, ticket 11 is shown to have an opening 14 extending from the front face of ticket 11 rearwardly to a point short of the rear face of ticket 11. Thus, opening 14 is open only at its front face. Seated within opening 14 is a readout disk 140 containing indicating means for determining the presence of a specific analyte being sought by the process of one aspect of the present invention. A fold or score line 16 is present in ticket 11 at a set distance from opening 14. At a position in ticket 11 equally distant from score 16, a second opening 12 is located extending completely through ticket 11. Openings 14 and 12 are designed such that when ticket 11 is folded along score line 16, opening 12 and 14 will become coaxial with one opening overlaying the other opening.

Opening 12 contains an antibody disk 120 located within the front face portion, and a conjugate disk 121 located in the rear face portion. Thus, two separate disks 120 and 121 are located within opening 12. As shown in FIG. 3, opening 12 contains a generally annular ring 301 located generally midway through opening 12 and extending inwardly from the outer surface of opening 12 and having an upper stop surface 303 and a lower stop surface 302 upon which disks 120 and 121, respectively, may be fixed by adhesive or other means and held to ticket 11. However, it is to be understood that annular ring 301 is merely one embodiment by which disks 120 and 121 may be held in place within opening 12 of ticket 11, and that the actual means by which the disks are held in place is not critical to the present invention provided that such means do not interfere with the enzymatic assay being conducted. Thus, annular ring 301 may be omitted or modified if other alternative means such as "snap-fitting" or ultrasonic welding is used to obtain the desired result of holding the disk in place in opening 12. In such alternative embodiments, as well as the embodiment having an annular ring, conjugate disk 121 may be placed in direct contact with antibody disk 120 so long as equal competition of both free antigen and antigen/enzyme conjugate required for a competitive analysis, and subsequently that the direct repeatable transfer of liquid from the conjugate disk to the antibody disk is maintained and not untowardly affected.

For ease of use and as an indication that the proper amount of sample has been placed upon conjugate disk 121 for testing as described more fully below, conjugate disk 121 is set into ticket 11 a sufficient distance to form an open sample well 304 defined by the depth of the interior cylindrical wall of opening 12 and the upper surface of disk 121. In manufacturing an enzyme reagent ticket according to the present invention, the sample well 304 is preferably designed to have a volume equal to or greater than that necessary for the aliquot of the test sample to be assayed. In addition, either the ticket (which may be manufactured from a number of different materials such as paper or plastics such as poylethylene or polypropylene) or the interior of the sample wells may be coated with a material which will prevent non-specific binding to the surface of the ticket or well thereby resulting in false results. Thus, in use, the proper amount of sample necessary to conduct the desired assay may be provided merely by filling the sample well to capacity. Similarly, the proper amount of control sample may also be placed in a similar sample well in opening 13 to allow an unknown sample to be tested against a known control sample.

In general use, an aliquot of sample is placed in well 304 (or upon conjugate disk 121) and an aliquot of control sample is placed in similar fashion on a similar conjugate disk 131 in opening 13. The samples are allowed to flow through their respective conjugate disks and subsequently be absorbed into their respective antibody disks. The ticket is then folded along seam 16 placing the sample antibody disk 120 directly over the sample readout disk 140 and control antibody disk 130 directly over the control readout disk 150. The ticket is then squeezed together to express any unbound analyte/enzyme conjugate into the readout disk containing an indicator means such as a chromophore which will undergo a change indicative of the presence, and lower limit, of the specific analyte being assayed.

One use for the enzyme reagent ticket according to the present invention is in an immunochemical assay for T-2 toxin. T-2 toxin is a trichothecene mycotoxin produced by *Fusaruim sp*. This fungal toxin is commonly found in cereal grains such as corn and wheat and results in large amounts of contaminated grain to be destroyed annually. It is also a potential biological warfare and terrorism agent which has been reported to have been used as late at the 1980's. Chemically, it is a multi-ring structure of the following formula:

The toxin has an $LD_{50}$ for mice at 0.15 to 6.1 mg/kg of body weight depending upon the route of administration, and results in necrosis, vomiting, the inhibition of protein synthesis, and it is also suspected as being a carcinogen. Currently, the presence of the toxin is most often determined by gas chromatography, high-performance liquid chromatography, and mass spectrophotometry. Using the enzyme reagent ticket according to the present invention to determine the presence of this toxin in samples presents a number of apparent advantages over the present non-mobile devices used to assay for this toxin.

In manufacturing an enzyme reagent ticket according to the present invention for use in determining the presence, lower limit, and approximate amount of T-2 toxin present in a sample, the conjugate, antibody and readout pads or disks are manufactured incorporating the reagents for the assay. Each of the pads or disks are manufactured from a sheet of stock material from which the disks will be formed or from preformed disks previously cut from the stock material. The stock material or preformed disks are manufactured using wet reagent chemistry application to the material or disks and subsequently drying the material or disks in, for example, a vacuum oven. When manufacturing is complete, the reagent tickets or kits are preferably stored until use in desiccated air-tight packets.

The conjugate pad is manufactured as a physical and nonreactive support for the T-2 toxin conjugated to glucose oxidase. In a preferred methodology for the manufacture of this pad, the T-2 toxin is first activated with sulfo-NHS, and the glucose oxidase is linked to RNase by periodate conjugation following conventional techniques. The RNase serves as a spacer between the toxin and glucose oxidase when these two components are allowed to react. Thus, the final conjugate may be analyte/sulfo-NHS/RNase/glucose oxidase, or another suitable analyte/linker/glucose oxidase, wherein the analyte in the present descriptive embodiment is T-2 toxin. The quantity of the T-2/glucose oxidase conjugate required is best determined on a batch by batch basis depending upon the activity of the glucose oxidase reagent. In applications for other analytes the relationship between the quantity of conjugate and the quantity of appropriate antibody supported in the antibody disk will vary somewhat and need to be optimized for the specific application using conventional techniques. Very briefly, one such technique requires the addition of 100 μL aliquots of antibody protein ranging from 10 to 100 μg/mL in 10 μg increments to the antigen and measuring the degree of binding; the point at which maximum antigen binding occurs per mg of antibody protein is regarded as the optimum antibody concentration for use with the enzyme reagent ticket according to the present invention. In one embodiment with T-2 analyte, 0.012 glucose oxidase units in 0.01M HEPES buffer was adjusted to pH 7.8 and applied to the pad. More specifically, the T-2/glucose oxidase conjugate for application to the conjugate pads according to the present invention is prepared according to the following example:

EXAMPLE I

Sephadex G25™ was swelled in phosphate buffered saline and degassed for at least 15 minutes. A chromatographic column, 43 to 45 cm high and 2.5 cm wide, was packed with the swelled Sephadex G25™, flushed and equilibrated with phosphate buffered saline buffer. The column can be reused several times if washed with sodium azide or thimersol and stored at 4° C. when not in use.

The glucose oxidase solution was prepared by dissolving glucose oxidase in phosphate buffered saline to a final concentration of 3.336 mg protein/ml. 600 μL of the solution and 1400 μL of sodium bicarbonate buffer (2.0M) are added to 5.5 mg of T-2 sulfo-NHS with constant stirring. Sulfo-NHS chemically is N-hydroxysulfosuccinimide and is used to activate T-2 toxin in order to facilitate linking to RNase, other linkers, or glucose oxidase. The T-2 sulfo-NHS was allowed to dissolve, the pH adjusted to 9.0 with sodium carbonate (2.0M), and the solution was stirred for an additional 45 minutes at room temperature. The solution was passed through a filter with pore size of 0.45 μm or smaller and applied to the Sephadex G25™ column. Fractions of 1 mL were eluted from the column with phosphate buffered saline buffer. Fractions containing the T-2 sulfo-NHS-glucose oxidase conjugate were identified by absorbance at 450 nm, pooled, concentrated to 1 or 2 mL using suitable ultrafiltration techniques, and assayed for glucose oxidase activity. The conjugate was stored at 4° C. until used (if stored for extended periods, the conjugate should, of course, be assayed prior to use).

With regard to the pad stock used in the manufacture of the conjugate pad, this may be selected from a wide range of materials. However, stock of rayon or nylon are materials of choice because of the ability of these materials to support the glucose oxidase/T-2 conjugate separate from the antibody in the pad or disk positioned immediately adjacent it. When the sample is added to the conjugate disk (as for example pad 121 in FIG. 3), the glucose oxidase/T-2 conjugate and any toxin present in the sample mix freely. Furthermore, with these materials of choice, liquid retention is negligible as a result of negligible absorptive qualities of the material; these materials provide for virtually 100% transfer of the sample and glucose oxidase/T-2 conjugate (i.e. the conjugate is mobilizable by sample) into the antibody disk.

Two monoclonal antibodies (15H6 and 12C12) to T-2 toxin have been produced for use in the one aspect of the present invention involving the detection of T-2 toxin. However, the use of specific monoclonal antibodies is not a necessity for the present invention, and any antigen-specific antibody should be adequate for the determination of a desired analyte by the device of the present invention. However, no matter which type of antibody—monoclonal or polyclonal—is used, the ratio of conjugate to antibody should be optimized for the specific antibody and its characteristic binding capacity. The antibody pad is prepared by applying a quantity of antibody to the antibody disk. For example, in one embodiment of the present invention, 0.025 mg of 15H6 monoclonal antibody protein in 50 μL of 0.01M HEPES buffer adjusted to a pH of 7.8, was applied to each disk.

With regard to the pad stock used in the manufacture of the antibody pad, this may be selected from a wide range of fibrous or porous materials capable of supporting the antibody such as cellulose, glass, fabric, plastic, or plastic coated cellulose, plastic coated glass, plastic coated fabric, and mixtures of the same. For example disks may be manufactured from stock such as Whatman 17 filter paper which has been activated with 1,1'-carbonyldiimidazole in dioxane; monoclonal antibodies are then bound to the activated pads in 0.1M borate buffer and dioxane. Because antibodies are known to bind passively to polystyrene microtiter plates commonly used in such immunoassay procedures as ELISA, polystyrene coating of the paper stock may also be used as a milder and more effective method of binding the antibodies to the pad. In this embodiment, the polystyrene (or other plastic material, such as PVC, capable of binding antibodies) is first dissolved in a solvent such as chloroform. The paper stock is then wetted with the plastic solution and allowed to dry. One such method for the manufacture of the antibody pad according to the present invention applied approximately 30 μL of a 4.5 mg/ml polystyrene in chloroform solution to each cellulose pad. The pads are removed from the solution and allowed to dry. After drying, a stock solution containing the antibody may be applied to the pad. These conditions not only optimize the shelf-life of the monoclonal antibodies, but also the specific binding reaction of T-2 toxin by the 15H6 monoclonal antibodies required for an accurate diagnosis. More specifically, the antibody pads are prepared according to the following example:

EXAMPLE II

Polystyrene resin was dissolved in sufficient chloroform solvent to obtain a concentration of 4.5 mg of polystyrene per each milliliter of solvent. A 30 μL aliquot of the polystyrene solution was applied to each ⅝ inch Whatman 17 pad and allowed to air-dry under a chemical hood for 30 minutes. The dried pads were then transferred to a convection oven at 70° C. for 30 minutes, removed, and allowed to cool to ambient temperatures.

Monoclonal antibody (15H6) was diluted in 0.01M HEPES buffer at a pH of 7.8 to a final protein concentration of 0.5 mg/mL. 50 μL of the antibody solution was applied to each polystyrene pad, the pads were covered to prevent dehydration, and incubated at 4° C. for 12 to 18 hours.

The pads were then placed in a 1% (w/v) solution of lysine in 0.01M HEPES buffer at pH 7.8 and gently agitated for 1 hour. The use of lysine (or other low molecular weight blocking agents) as a "blocking agent" is important to the technical success of this procedure since the lysine acts to coat any pad surface not coated by antibody, and thus prevents subsequent non-specific protein binding. The use of lysine is especially attractive since it is not believed to increase steric hindrances that may occur with larger molecular weight blocking agents such as BSA, which may influence the binding of toxin and antibody.

The lysine solution is decanted from the pads and the pads are washed in 0.01M HEPES buffer at pH 7.8 to remove any excess lysine. The pads are then dried under full vacuum at 25° C. for 4 hours followed immediately by 1 hour under full vacuum at 88° C. The pads are stored desiccated closed containers until such time as the reagent tickets according to the present invention are manufactured.

The readout pad is prepared by applying a quantity of indicator reagent to the disk. For example, in one embodiment of the present invention, 20 μL of indicator solution containing 2,2'-azino-di-(ethyl-benzthiazolinsulfonate) (ABTS), glucose, and horseradish peroxidase (1.2 mg/mL, 240 mg/mL, and 0.55 mg/mL, respectively) in 0.05M piperazine-N,N'-bis(2-hydroxypropanesulfonic acid) (POPSO) buffer adjusted to pH 7.0, was applied to each filter (Schleicher & Schuell GB002 was used as one embodiment of the present invention) readout pad.

The design of the enzyme reagent ticket described above for detection of T-2 toxin relies upon two separate enzyme systems. The first enzyme, glucose oxidase (GO) is conjugated to the target through a spacer; the second enzyme, horseradish peroxidase is used as the indicator enzyme. In the presence of the component sought, T-2 toxin, some of the T-2/GO conjugate passes through the antibody pad without being bound and reacts with its substrate, glucose, to produce peroxide. The horseradish peroxidase reacts with the peroxide to produce water and singlet oxygen free radical which in turn oxidizes the chromogen [2,2'-azino-di-(ethylbenzthiazolinsulfonate)] (ABTS) to produce a blue to green color. These reactions may be depicted as:

β-D-glucose+T-2/GO-FAD→T-2/GO-FADH$_2$+gamma-D-gluconolactone

T-2/GO-FADH$_2$+O$_2$→T-2/GO-FAD+H$_2$O$_2$

H$_2$O$_2$+horseradish peroxidase→H$_2$O$_2$-HRP

H$_2$O$_2$-HRP+4-aminoantipyrine (AAP)→H$_2$O$_2$-HRP-AAP

H$_2$O$_2$-HRP-AAP+ABTS (colorless)→H$_2$O+HRP+AAP+oxidized ABTS (blue)

Thus, in using the enzyme reagent ticket according to the present invention for the determination, for example, of T-2 toxin, an amount of sample (43–47 μL) is added to conjugate pad 121 (and a known amount of T-2 toxin is added to conjugate pad 131) of the FIG. 1 embodiment or to conjugate pad 240 of the FIG. 2 embodiment. Any T-2 toxin present in the sample will become homogeneously mixed with the T-2/GO conjugate on the conjugate disk. The liquid sample added to conjugate disk 121 passes through the pad into the antibody disk 120 due to gravity and the much greater absorptivity of the antibody pad as compared to the conjugate pad. In the FIG. 2 embodiment, ticket 21 is folded along line 24a to bring the conjugate pad 240 in section 1 over the antibody disk 230 in section 2 (see FIG. 2B) and the liquid in the conjugated pad is squeezed or otherwise expressed into the antibody pad 230. Once this is done, ticket 21 is opened (see FIG. 2C). In both embodiments the fluid in the antibody pad 120 or 230 is allowed to react for approximately two minutes. In both the FIG. 1 and FIG. 2 embodiments, free T-2 toxin and T-2/GO conjugate compete for a limited number of antibody sites which equal the number required to bind all the T-2/GO conjugate. Any free T-2 toxin in the sample will therefore overload the system so that some free T-2 and T-2/GO conjugate will remain unbound by the antibody. The antibody pad 120 or 230 is then brought in contact with the readout pad 140 or 220 respectively by folding ticket 11 along score line 16 or by folding ticket 21 along score line 24b. The folded ticket is squeezed once again to express fluid into the readout pad allowing any GO in the T-2/GO conjugate-containing fluid transferred to the readout pad to react with the glucose in the readout pad. In the presence of water, hydrogen peroxide will be produced and becomes the substrate for horseradish peroxidase. In the indicator system as defined, HRP catalysis of hydrogen peroxide yields water and free oxygen. The free oxygen radical is transferred to reduced ABTS (in this state ABTS is colorless) and results in the oxidation of ABTS to a green to blue color within about ten minutes. The change of color, therefore is an indicator of the presence, lower limit, and approximate amount of T-2 toxin contained in the original sample. Confirmation of both a valid test and the amount of T-2 present in the sample is made comparing the test readout pad 140 with the positive control readout pad 150.

In addition to the use of GO and ABTS, other indicator systems may also be used. Among these additional systems are, for example, acetyl cholinesterase which catalyzes the hydrolysis of indoxyl acetate to indole resulting in a blue indicator system; butyryl cholinesterase which produces a blue color by catalyzing the hydrolysis of 2,6-dichloroindophenyl acetate to 2,6-dichloroindolphenol and acetic acid; alkaline phosphatase which catalyzes the hydrolysis of 5-bromo-4-chloro-3-indolyl phosphate to the indole which when added to nitro blue tetrazolium chloride produces a dark purple color; and β-galactosidase which produces a dark gold color upon the hydrolysis of o-nitrophenyl-β-D-galactopyrannoside. Each of these four enzyme systems has been previously used and proven in numerous immunoassays as highly reliable and stable indicator systems.

In addition to the use of the enzyme reagent ticket of the present invention in determining the presence of T-2 toxin, the presence of a wide variety of compounds can be determined utilizing modified enzyme reagent tickets according to the present invention. For example, the enzyme reagent ticket according to the present invention may be used, with the appropriate conjugate and antibody disks in place, to determine the presence of morphine group alkaloids such as morphine, codeine, and heroin; cocaine group alkaloids such as ecgonine; cinchona group alkaloids such as quinine; isoquinoline group alkaloids such as mescaline; ergot group alkaloids such as lysergic acid; steroids such as estrogens, androgens, adrenocortical hormones, bile acids, and saponins; vitamins; polypeptides and proteins; barbiturates; environmetally hazardous compounds; infectious agents; and various pharmaceuticals. In addition to testing body fluids, samples may be taken from other sources such as, for example, surfaces, gases, residues, liquids, and clothing. In those instances where the sample is in the form of powders or other non-liquid structure, it will be necessary to dissolve or extract the sample in an appropriate solvent prior to testing.

Thus, while I have illustrated and described the preferred embodiment of my invention, it is to be understood that this invention is capable of variation and modification, and I therefore do not wish to be limited to the precise terms set forth, but desire to avail myself of such changes and alterations which may be made for adapting the invention to various usages and conditions. Accordingly, such changes and alterations are properly intended to be within the full range of equivalents, and therefore within the purview of the following claims.

Having thus described my invention and the manner and a process of making and using it in such full, clear, concise and exact terms so as to enable any person skilled in the art to which it pertains, or with which it is most nearly connected, to make and use the same;

I claim:

1. An enzyme immunoassay device for use in determining the presence of an analyte in a sample which comprises:
   i) a planar support comprising an upper surface and a lower surface and further comprising a fold means defining a first and a second support half by which the upper surface of the device may be folded together along said means;
   ii) a first opening in the first support half (a) spaced a defined distance from the fold means, (b) extending through the support, and (c) defining a sample well comprising an interior being opened at the lower surface of the support and closed at the upper surface of the support with a closure comprising a conjugate pad of negligible liquid absorptive qualities facing the interior of the sample well, said conjugate pad containing a mobilizable immunoreactant comprising said analyte conjugated to an enzyme; and an antibody pad having greater liquid absorptivity than said conjugate pad, comprising an immobilized antibody that specifically binds to said analyte, and located axial to the conjugate pad and at the upper surface of the support; and
   iii) a second opening located at the upper surface of the second support half (a) spaced an equal distance to the first opening from the fold means, (b) extending partially through the support, and (c) containing a readout pad comprising a chromophoric indicator means that reacts with said enzyme to produce a color change, and wherein the antibody and readout pads will be in contact with each other when the support is folded along the fold means.

2. A device according to claim 1 wherein the immunoreactant is conjugated to the enzyme through a RNase linker.

3. A device according to claim 1 wherein the antibody pad farther comprises a blocking agent bound to binding sites on said pad which are not bound to the antibody.

4. A device according to claim 1 wherein the antibody pad is fibrous and wherein the fibers are selected from the group consisting of cellulose, glass, fabric, plastic, plastic coated cellulose, plastic coated glass, plastic coated fabric, and mixtures of the same.

5. A device according to claim 4 wherein the antibody pad antibody is a monoclonal antibody immunologically reactive with said analyte.

6. A device according to claim 5 wherein the analyte is T-2 toxin.

7. A device according to claim 5 wherein the plastic is polystyrene.

8. A device according to claim 2 wherein the analyte is T-2 toxin.

9. A method for utilizing an enzyme immunoassay device for determining the presence of an analyte in a liquid sample which comprises:
   i) providing said sample;
   ii) providing a device according to claim 1 wherein the conjugate pad is a disk of fibers with negligible absorptive properties, the immunoreactant comprises the analyte conjugated to a first enzyme, the antibody pad is a disk containing the immobilized antibody, and the readout pad is a disk containing the chromophoric indicator;
   iii) adding the sample to the conjugate disk;
   iv) allowing said sample to flow through the conjugate disk to mobilize and to transport the immunoreactant into the antibody disk wherein both said immunoreactant and the analyte in said liquid sample are competitively bound by said immobilized antibody;
   v) folding said device along said fold means;
   vi) expressing said sample from the antibody disk into the readout disk wherein said chromophoric indicator, comprising a substrate for said first enzyme and second enzyme that reacts with a product produced by said first enzyme to yield a change in color, reacts with said first enzyme in any immunoreactant not bound by said immobilized antibody; and
   vii) noting the presence of any change in the color of the indicator which change indicates the presence of said analyte in said sample.

10. A method according to claim 9 wherein step iii) further comprises:
    i) placing the support in a configuration wherein the sample flows from the conjugate disk into the antibody disk; and
    wherein the analyte is T-2 toxin, the first enzyme is glucose oxidase, and the second enzyme is horseradish peroxidase.

11. An enzyme immunoassay device for use in determining the presence of an analyte in a sample which comprises:
    i) a planar support comprising an upper surface and a lower surface and further comprising a fold means defining two halves of the support and by which the upper surface of the support halves may be folded upon itself;
    ii) (a) a first opening in the first half of the support spaced a defined distance from the fold means and extending through the support, (b) a conjugate pad containing a mobilizable immunoreactant comprising said analyte conjugated to an enzyme, said pad having negligible liquid absorptive qualities and located within said opening and at the lower surface of the support, and (c) an antibody pad having greater liquid absorptivity than said conjugate pad and having an immobilized antibody that specifically binds to said analyte and located at the upper surface of the support and axial to the conjugate pad;
    iii) a readout pad comprising a chromophoric indicator means that reacts with said enzyme to produce a color change located at the upper surface of the second half of the support and equal in size to the opening in the first half and spaced equally to the first half opening from the fold means, and wherein said readout pad and said first opening are coplanar to a plane passing at right angles through said support and said fold means.

12. A device according to claim 11 wherein said readout pad is within an opening in said second half which opening does not extend completely through the support.

13. A device according to claim 11 wherein the antibody is selected from the group consisting of monoclonal and polyclonal antibodies immunologically reactive with the analyte.

14. A device according to claim 13 wherein the antibody is immunoreactive with T-2 toxin.

15. A device according to claim 13 wherein the antibody pad is fibrous and wherein the fibers are selected from the group consisting of cellulose, glass, fabric, plastic, plastic coated cellulose, plastic coated glass, plastic coated fabric, and mixtures of the same.

16. A device according to claim 13 wherein the analyte is T-2 toxin.

17. A device according to claim 11 wherein the conjugate pad is inward of the lower surface of the support thereby forming a sample chamber comprising the surface of the conjugate pad and the interior walls of the opening extending from the conjugate pad to the lower surface of the support.

18. An enzyme immunoassay device for use in determining the presence of an analyte in a sample which comprises:
   i) a planar support comprising an upper surface and a lower surface and having first, second and third sections defined by a first fold means between said first and second sections, and a second fold means between said second and third sections, by which the upper surfaces of each section may be folded along said means upon its adjacent section;
   ii) a first opening in said first section spaced a defined first distance from said first fold means and partially extending through the support; said opening containing a conjugate pad of negligible liquid absorptive qualities and containing a mobilizable immunoreactant comprising said analyte conjugated to an enzyme;
   iii) a second opening in said second section spaced a defined second distance from said first fold means equal to said first distance, said opening partially extending through said support and containing an antibody pad having greater liquid absorptivity than said conjugate pad and comprising an immobilized antibody that specifically binds to said analyte;
   iv) a third opening in said third section spaced a defined third distance from said second fold means equal to said second distance, said third opening extending partially through said support and containing a readout pad having a chromophoric indicator means that undergoes a color change in the presence of said analyte conjugated to said enzyme; and
said first second and third openings being aligned along a common axis so that when said first and second sections are folded along said first fold means said first and second openings will coincide with each other, and so that when said second and third sections are folded along said second fold means said second and third openings will coincide with each other.

19. An enzyme immunoassay to determine the presence of an analyte in a liquid sample which comprises:
   (A) placing said sample in contact with a conjugate pad carried by an enzyme immunoassay device which comprises:
      i) a planar support comprising an upper surface and a lower surface and having first, second and third sections defined by a first fold means between said first and second sections, and a second fold means between said second and third sections, by which the upper surfaces of each section may be folded along said means upon its adjacent section;
      ii) a first opening in said first section spaced a defined first distance from said first fold means and partially extending through the support; said opening containing a conjugate pad of negligible liquid absorptive qualities and containing a mobilizable immunoreactant comprising said analyte conjugated to an enzyme;
      iii) a second opening in said second section spaced a defined second distance from said first fold means equal to said first distance, said opening partially extending through said support and containing an antibody pad having greater liquid absorptivity than said conjugate pad and comprising an immobilized antibody that specifically binds to said analyte;
      iv) a third opening in said third section spaced a defined third distance from said second fold means equal to said second distance, said third opening extending partially through said support and containing a readout pad having a chromophoric indicator means that undergoes a color change in the presence of said analyte conjugated to said enzyme; and
   said first, second and third openings being aligned along a common axis so that when said first and second sections are folded along said first fold means said first and second openings will coincide with each other, and so that when said second and third sections are folded along said second fold means said second and third openings will coincide with each other;
   (B) folding said first and second sections along said first fold means to bring said conjugate and antibody pads together and expressing said liquid from said conjugate pad to said antibody pad;
   (C) folding said second and third sections along said second fold means to bring said antibody and readout pads together and expressing said liquid from said conjugate pad to said readout pad; and
   (D) determining the presence or absence of a color change of said readout pad.

20. A method for manufacturing an enzyme immunoassay device for use in determining the presence of an analyte in a sample which comprises:
   i) providing a sheet stock of support material comprising (a) an upper and lower surface, (b) fold means defining said support into two halves, and (c) providing an opening extending through one of said halves defined by said fold means;
   ii) providing a first pad having negligible liquid absorptive qualities and having a mobilizable immunoreactant comprising an enzyme conjugated to said analyte and placing said first pad into said first opening at the lower surface of the support;
   iii) providing a second pad having greater liquid absorptivity than said first pad and having an immobilized antibody capable of specifically binding to said analyte supported thereon and placing said second pad into said opening at the upper surface of the support; and
   iv) providing a third pad having a chromophoric indicator means comprising a substrate reactive in the presence of the enzyme of said immunoreactant in said first pad and placing said third pad at the upper surface of said stock.

21. The method of claim 20 which further comprises providing fold means midway between said opening and said third pad.

22. A method for manufacturing an enzyme immunoassay device for use in determining the presence of an analyte in a sample which comprises:
   i) providing a sheet stock of support material comprising an upper and lower surface, ii) providing fold means in said material dividing said material into a first half and a second half, and further providing an opening extending through said first half of said material;

iii) locating a first pad with negligible liquid absorptive qualities and having a mobilizable immunoreactant comprising the analyte conjugated to an enzyme in said first opening at the lower surface of the support to form a sample chamber with the interior walls of said opening;

iv) providing a second pad having greater liquid absorptivity than said first pad and having an immobilized antibody capable of specifically binding to said analyte thereon, and placing said second pad in overlay contact with said first pad; and v) placing a third pad having a chromophoric indicator means that will undergo a color change in the presence of said immunoreactant, said chromophoric means being placed at the upper surface of the second support half and corresponding in size to the size of the second pad and spaced an equal distance to the opening in the first support half from the fold means, wherein said second and third pad will be in contact with each other when the device is folded along the fold means.

* * * * *